(12) United States Patent  
Siebenkotten et al.

(10) Patent No.: US 7,704,727 B2
(45) Date of Patent: Apr. 27, 2010

(54) DEVICE AND METHOD FOR PROCESSING BIOLOGICAL MATERIAL

(75) Inventors: Gregor Siebenkotten, Frechen-Königsdorf (DE); Herbert Müller-Hartmann, Köln (DE); Gudula Riemen, Langenfeld (DE); Günter Kraus, Pulheim (DE)

(73) Assignee: Lonza Cologne AG (DE)

( * ) Notice: Subject to any disclaimer, the term of this patent is extended or adjusted under 35 U.S.C. 154(b) by 1174 days.

(21) Appl. No.: 10/527,958

(22) PCT Filed: Sep. 12, 2003

(86) PCT No.: PCT/DE03/03042

§ 371 (c)(1),
(2), (4) Date: Sep. 12, 2005

(87) PCT Pub. No.: WO2004/027015

PCT Pub. Date: Apr. 1, 2004

(65) Prior Publication Data

US 2006/0160221 A1    Jul. 20, 2006

(30) Foreign Application Priority Data

Sep. 16, 2002    (DE) .............................. 102 43 086

(51) Int. Cl.
*C12M 1/42*        (2006.01)
*C12N 15/87*       (2006.01)

(52) U.S. Cl. .............. 435/285.2; 435/173.6; 435/287.6; 435/461; 204/453

(58) Field of Classification Search .............. 435/173.6, 435/285.2, 461, 173.4, 173.5, 470, 287.6; 204/453, 196.13, 516; 800/292; 422/82.03, 422/93
See application file for complete search history.

(56) References Cited

U.S. PATENT DOCUMENTS 3,521,745 A  *  7/1970  Schwartzman .............. 206/222
4,061,543 A  *  12/1977  Bean et al. ..................... 435/32
4,441,972 A      4/1984  Pohl
4,699,881 A     10/1987  Matschke (Continued)

FOREIGN PATENT DOCUMENTS

DE             33 17 415 A1    11/1984

(Continued)

*Primary Examiner*—William H Beisner
*Assistant Examiner*—Michael Hobbs
(74) *Attorney, Agent, or Firm*—Joyce v. Natzmer; Pequignot + Myers

(57) ABSTRACT

Disclosed is a device for processing biological material which at least comprises a chamber at least closable to the outside and having an inner space for receiving the biological material. The chamber comprises at least one electrode placed in contact with the inner space for generating an electric field. Also disclosed is a method for processing biological material. The biological material is introduced into the inner space above and the electrode can generate an electric field after said biological material is introduced by applying voltage to said electrode and a further electrode in contact with the inner space. The chamber comprises at least one inlet line having at least one opening arranged close to the electrode. The biological material is almost completely rinsed out of the inner space after the electric field is generated, via a solution guided via an inlet line of the chamber along at least one electrode.

31 Claims, 5 Drawing Sheets

U.S. PATENT DOCUMENTS

| | | | |
|---|---|---|---|
| 4,764,473 A | 8/1988 | Matschke et al. | |
| 4,849,089 A | 7/1989 | Marshall | |
| 4,968,567 A * | 11/1990 | Schisselbauer | 429/90 |
| 5,641,680 A | 6/1997 | Zhao | |
| 6,720,178 B1 * | 4/2004 | Berson et al. | 435/298.2 |
| 2002/0164776 A1 | 11/2002 | Beichmann et al. | |
| 2003/0190608 A1 * | 10/2003 | Blackburn | 435/6 |
| 2004/0029266 A1 * | 2/2004 | Barbera-Guillem | 435/297.5 |

FOREIGN PATENT DOCUMENTS

| | | |
|---|---|---|
| DE | 35 22 610 A1 | 12/1986 |
| EP | 0 128 566 A2 | 12/1984 |
| JP | 63049070 A | 3/1988 |

* cited by examiner

US 7,704,727 B2

DEVICE AND METHOD FOR PROCESSING BIOLOGICAL MATERIAL

This is the U.S. national stage of International application PCT/DE2003/003042, filed Sep. 12, 2003, designating the United States, which claims priority to German application DE102 43086.1, filed Sep. 16, 2002. These applications are incorporated herein by reference in their entirety.

FIELD OF THE INVENTION

The invention relates to a device for treating biological material, which at least comprises a chamber which at least can be closed in relation to the outside and which comprises an inner space for receiving said biological material, wherein said chamber comprises at least one electrode which is placed in contact with said inner space of said chamber and is provided for generating an electric field. The invention further relates to a method for treating biological material, wherein said biological material is introduced into the inner space of a chamber which at least can be closed in relation to the outside and which comprises at least one electrode which is placed in contact with said inner space of said chamber and is provided for generating an electric field which is generated in said inner space after introducing said biological material by applying voltage to said electrode and a further electrode which is in contact with said inner space of said chamber.

BACGROUND OF THE INVENTION

Transferring biologically active molecules, such as, for example, DNAs, RNAs or proteins, into living cells is an important tool for analysis of biological functions of these molecules. Electroporation is a preferred method for transferring foreign molecules into the cells, which in contrast to chemical methods does not depend on a simultaneous transport of other biologically active molecules. During electroporation the foreign molecules are introduced into the cells from a buffer solution adapted to the cells or a cell culture medium by a short-time current flow, whereby the cell membrane is made permeable for the foreign molecules by effect of the short electric pulses. The cell suspension is usually provided in a so-called cuvette, i.e. a small container which is open at the top and which comprises two parallel and oppositely arranged electrodes disposed in the sidewalls near the bottom and serving for the application of electric voltage. Through the temporarily emerging "pores" in the cell membrane the biologically active molecules initially reach the cytoplasm where they eventually already exert their function to be analysed. At certain conditions the molecules subsequently also enter the nucleus of the cell.

Due to the temporarily applied intensive electric field, i.e. a short pulse with high current density, cells, derivatives of cells, subcellular particles and/or vesicles can also be fused. During this so-called electrofusion at first, for instance, the membranes of the cells are brought in close contact by an inhomogenous alternating electric field. The subsequent application of an electric field pulse leads to an interaction of parts of the membranes finally leading to cell fusion. Comparable devices such as the ones used for electroporation can be used for electrofusion as well.

Containers as mentioned above are known and primarily used for electroporation or electrofusion in the form of cuvettes having inserted electrodes made of metal. Containers used for this purpose are mostly small vessels which are closed at the bottom and open at the top and whose inner space is built by two pairs of parallel and oppositely arranged sidewalls. The inner space serves for receiving of the cell suspension, i.e. usually an aqueous buffer solution or a cell culture medium, in which the cells to be treated are suspended. Such cuvettes mostly comprise a pair of electrodes for application of an electric voltage disposed near the bottom of a pair of oppositely arranged sidewalls. During an electric discharge an electric current flows through the cell suspension between both electrodes, which enables an introduction of nucleic acids or other molecules into the cells or, depending on the selected conditions, leads to fusion of cells. The electrodes are mostly made of metal, wherein aluminium is frequently used.

For example, a chamber for treating cells in an electric field is known from German Patent DE 33 21 239 C2, which has an inner space for receiving of a suspension comprising living cells, wherein at least two electrodes each project into said inner space. As usual, these electrodes serve for application of voltage in order to generate an electric field between said electrodes, wherein the cells are exposed to said electric field. Though the chamber is provided for cell fusion, it may also be used for transferring of nucleic acids into cells, i.e. the so-called electroporation. The inner space of the chamber is hermetically sealed at all sides, wherein one area of the wall surrounding said inner space can be perforated by a needle or canula. Thus, the wall may partially comprise a foil made of acetyl cellulose, which can be perforated. The cell suspension can be poured in the chamber and removed therefrom through this perforatable foil. This is beneficial because treating of the cells may occur under aseptic conditions. However, after treating the cells, the chamber can only be rinsed circumstantially and unsatisfactory so that always a remarkable portion of treated cells remains in the inner space of the chamber.

A chamber for treating cells in an electric field is also known from German Patent DE 33 17 415 C2. With this chamber, the inner space is limited by an inner body and an outer casing which surrounds the longitudinal axis of the inner body equally distanced. The electrodes projecting into the inner space surround the inner body in the form of a multi-threaded screw having an equal lead. The chamber has a sealable inlet line for introducing the cell suspension and a sealable outlet line for removing the cell suspension. Thus, this chamber may be used as flow through chamber as well. In this case, a predetermined amount of cell suspension is pressed or sucked into the chamber, electric treatment is then carried out, and finally the cell suspension located in the chamber is pressed or sucked out of the chamber and replaced by a new amount of cell suspension. After electric treatment of the cells, the inner space can be rinsed with a cleaning solution which may be pressed into the inner space via a pore system. However, also in this embodiment, effective flushing of the chamber after electric treatment of the cells without the use of a cleaning solution, i.e. under preservation of the viability of the cells, is not possible as the solution cannot flow along the entire surface of the electrodes with high flow rate.

A further chamber for treating cells in an electric field is known from German Patent DE 35 22 610 C2, wherein the walls building the inner space for receiving the cell suspension consist of an inner and an outer electrode. The chamber includes an opening for introducing the cell suspension, which is closed by a plug, and an outlet opening for removing treated cells. A defined amount of suspension may be introduced into the inner space using a pipet and subsequently treated electrically. By introducing an additional exactly dosed amount of solution the cell suspension is then pressed downward through the outlet opening out of the inner space.

Due to the geometry of the chamber and the arrangement of electrodes in the form of an inner and outer electrode, it is also not feasible to rinse the treated cells with high flow rate.

U.S. Pat. No. 4,849,089 describes a chamber for electrcally treating vesicles, which is formed by a circular collar. The inner space for holding the suspension of vesicles is built by an inner ring which is spaced from the collar. The isolating material disposed between the collar and the inner ring is broken through by two passageways which render the inner space accessible from the outside. The suspension may be filled in or removed from the inner space through these passageways. The electrodes each consist of circular plates which are placed in the collar from above and the bottom, and which form the bottom plate and the top cover of the inner space, respectively. Also with this device, due to the circular geometry of the inner space and the electrodes situated at top and bottom an effective flow-through and hence completely rinsing the treated vesicles is not feasible.

It is a drawback of all devices and methods for electroporation and electrofusion known by now that the treated cells or vesicles can only be removed from the chamber incompletely, i.e. with relatively high loss of biological material. In particular, if the voltage pulses used have a very high field strength, i.e. the electric field has a high current density, cell material often deposits on the electrodes, primarily on the cathode. Additionally, intense gas formation often occurs leading to foam formation what also hampers the complete removal of treated cells.

SUMMARY OF THE INVENTION

It is therefore the problem to be solved by the invention to provide a device and method as initially mentioned, which avoid the drawbacks mentioned above and allow for recovery of treated cells from a chamber which is sealed to the outside as complete as possible.

According to the invention the above problem is solved by a device comprising a chamber which comprises at least one inlet line comprising at least one opening arranged close to said electrode. Due to this specific arrangement the inner space of said chamber can be effectively rinsed, even in a closed state and under aseptic conditions, wherein in particular the crucial region of the electrode is rinsed by the solution first. Thus, biological material adhering to inner surfaces of the chamber can be effectively removed leading to approximately complete recovery of the material employed. This is primarily beneficial with the use of valuable material which is only accessible in small amounts.

It is thereby advantageous if said inlet line is designed like a tube, i.e. has a minor cross section in proportion to its longitudinal extension. High flow rates within the inlet line and hence at its opening can be achieved in this configuration.

In an advantageous embodiment of the invention the inner diameter of said inlet line may be decreased in the direction of said electrode. This also leads to a high flow rate at the opening of the inlet line and thus to an effective rinsing operation. The diameter may thereby decrease gradually and continuously over the whole length of the inlet line or it may be limited to the region near the opening. In the latter case, the opening may be designed like a nozzle.

In a further embodiment of the invention it is provided that at least one reservoir for receiving a solution, which is built of a wall, is at least connectable to said inner space via said inlet line. This is particularly advantageous when the cells are not treated in a cell culture medium but in a buffer solution which is optimized for electrical treatment of cells. In this case, it is necessary to dilute the buffer solution with a solution which is adapted to the cells immediately after the end of the treatment. Due to the fact that the reservoir can be connected directly to the inner space it is ensured that the dilution of the buffer solution used during treatment is accomplished fast and uncomplicated.

The reservoir containing the solution for rinsing the chamber can be connected to the inner space, wherein said inner space of said chamber and said reservoir may be separated from each other by a separating unit, wherein said solution can be selectively introduced into said inner space of said chamber through said separating unit. This is primarily beneficial if the reservoir is firmly linked to the inner space since the solution shall not enter the inner space until the treatment of cells is finished. The separating unit may thereby be a valve or a fragile membrane which can be destroyed by applying pressure. In this embodiment, the chamber may be rinsed by simple manipulation from the outside what is primarily important under aseptic conditions.

For clinical applications which are accomplished under aseptic conditions it is provided that the chamber is at least aseptically sealed in relation to the outside. If the chamber shall be transported in the form of a closed unit that is pre-filled, for example, with a buffer solution, e.g. comprising solved biologically active molecules, the chamber may additionally be water-proof and/or gas-proof.

In an particularly advantageous embodiment of the invention, the wall building the reservoir may comprise an elastic and/or deformable material. Hereby, pressure can be applied from the outside to the solution situated within the reservoir so as to allow streaming of the solution into the inlet line at high flow rate. However, if in an alternative embodiment the solution is sucked out of the reservoir by negative pressure, the wall can deflate in proportion to the outpouring solution.

According to the invention, the reservoir may be at least connectable to the chamber. For example, said reservoir may be connected to said chamber building one piece so that both parts can be transported and used as one unit. But it may also be connectable to said chamber via a connecting member, preferably a Luer lock, so that both parts can be transported and stored separately. In the latter case, various reservoires which are already present with the user can be used with a chamber according to the invention. In an advantageous embodiment of the invention, said chamber and said reservoir form a unit which is at least aseptically sealed in relation to the outside.

In a particularly advantageous embodiment of the invention, it is provided that said chamber comprises at least one wall area which is self-sealing and can be perforated, preferably by a canula, and/or which is equipped with at least one inlet comprising a connecting member, preferably a Luer lock. It is for instance feasible to introduce a suspension of cells or other biological material into the inner space of said chamber through such wall area or a special connecting member under aseptic conditions.

Recovery of biological material can be further improved if the chamber has a minor cross-section and/or is formed like a serpent or spiral since this results in a high flow rate of the solution within the inner space.

In an alternative embodiment of the invention, the chamber may be divided in several subunits by at least one dividing member. Thereby, said dividing member may comprise a valve or a filter.

For receiving the treated biological material a container is provided, which is at least connectable to an outlet opening of said chamber, for example, connected to said chamber building one piece or connectable to said chamber via a connecting member, preferably a Luer lock. A partition member may be disposed between said chamber and said container. Said partition member is preferably a valve or a filter element. It is appropriate to choose the material of the filter element such that the treated biological material can pass the filter while bigger particles and complexes are retained. In this way, it can be avoided that objectionable components which were produced during electric treatment are present in the final product. This is primarily important with clinical use.

In an advantageous embodiment of the invention, the container comprises at least one wall area which is self-sealing and can be perforated, preferably by a canula. Alternatively, the container may be equipped with at least one outlet comprising a connecting member, preferably a Luer lock. Both embodiments allow easy and aseptic removal of the treated biological material from the container. Said container may also be, for example, a syringe or an infusion pot allowing the treated biologic material to be directly applied to a person to be treated, for example, in clinical practice.

Container and chamber may form a unit which is aseptically sealed in relation to the outside so as to be transported and stored in common.

The wall area of the chamber and/or the container, which is self-sealing and can be perforated comprises a synthetic material, for example a polysiloxane, an elastomer or rubber or a foil made of plastic. The foil could be made, for example, of acetyl cellulose.

In a preferred embodiment of the invention, said chamber comprises two oppositely arranged electrodes which are each placed in contact with said inner space.

Alternatively, a further electrode can be introduced into said inner space of said chamber.

Particularly preferred, said electrode or said electrodes comprise(s) an electroconductive synthetic material, preferably a plastic material which is doped with conductive material, so that no metal ions which are toxic for living cells can be emitted from said electrodes. This benefits the survival rate of cells when living cells, in particular eukaryotic cells, are treated.

According to the invention the above problem is solved by a method, wherein said biological material is almost completely rinsed out of said inner space of said chamber by means of a solution after said electric field is generated, said solution being guided via an inlet line of said chamber along at least one electrode. Thus, biological material adhering to inner surfaces of the chamber, in particular the electrode regions, can be effectively removed leading to approximately complete recovery of the material employed.

It is thereby advantageous if said solution is guided along said electrode at high flow rate.

Since biological material, in particular living cells, preferably adheres to the cathode, in a beneficial embodiment of the method according to the invention the solution is at first guided along the cathode.

In a further embodiment of said method, the biological material is introduced into said inner space of said chamber by means of a syringe or the like through a wall area which is self-sealing and can be perforated.

In an advantageous embodiment of said method, a separating unit is opened by extraneous mechanical impact, said separating unit separating said inner space of said chamber from a reservoir which contains said solution, said reservoir being connected or connectable to said chamber via said inlet line. In this manner, solution and chamber may be transported and stored together without unmeant contamination of the inner space by said solution. Thus, the inner space can be selectively rinsed, advantageously under aseptic conditions.

Additionally, the solution may be introduced into the inner space shortly after electric treatment so that a buffer solution that is adapted to electric treatment but less suitable for the biological material can eventually be diluted by said solution. The separating unit may thereby be a valve which can be opened by extraneous mechanical impact at least in one direction or a fragile membrane which can be destroyed by extraneously applied pressure. The fragile membrane is preferably made of a synthetic material, for example polyvinylene, polysterol, polyethylene oder foils made of cellulose. Thereby, the synthetic material may be coated with fluorohalocarbon which has a low permeability for water vapor and a good mechanical destructibility.

In a beneficial embodiment of said method, it is further provided that biological material and solution, respectively, are introduced into a container which is at least connectable to an outlet opening of said chamber. Using this container the treated material can then directly be provided for further use in a very simple manner.

In a further embodiment of the invention, a reservoir which contains said solution is at least partially formed by an elastic or deformable wall and a pressure is extraneously applied to said wall. In this manner, the solution is rinsed into the chamber under pressure leading to further improvement of efficiency of said method. Furthermore, the pressure applied may advantageously result in opening of the separating unit which separates the inner space of the chamber from the reservoir which contains the solution so as to easily break the separation under aseptic conditions.

The biological material may also be rinsed into said container through a partition member, in particular a valve or filter, which is disposed between said chamber and said container so as to accomplish rinsing selectively and/or with removal of perturbing components.

In particular in clinical practice it may be beneficial to remove the treated biological material from said container using a syringe or the like through a wall area which is self-sealing and can be perforated. Necessary sterility is hereby guaranteed, and additionally simple and direct use of the treated material is ensured.

In an alternative embodiment of said method, the biological material comprises living cells, preferably eukaryotic cells, derivatives of cells, subcellular particles or vesicles, into which biologically active molecules, preferably nucleic acids, are transferred by generation of said electric field, or which are fused by generation of said electric field.

Said biologically active molecules may already be solved in a buffer solution and introduced into the inner space of said chamber before the biological material is added. This measure significantly facilitates the method since merely biological material has to be added by the user.

In one embodiment of the invention, the transfer of said biologically active molecules into said living cells is achieved by a current density of up to 120 A/cm$^2$, preferably 80 A/cm$^2$, or by a voltage pulse having a field strength of 2-10 kV*cm$^{-1}$ and a duration of 10-200 µs.

In a further embodiment of the invention, the transfer of said biologically active molecules into said living cells is achieved by a current flow following said voltage pulse without interruption, said current flow having a current density of 2-14 A/cm$^2$, preferably 5 A/cm$^2$, and and a duration of 1-100 ms, preferably 50 ms.

BRIEF DESCRIPTION OF THE DRAWINGS

The present invention is further explained in detail by example of the figures.

DESCRIPTION OF VARIOUS AND PREFERRED EMBODIMENTS OF THE INVENTION

Figure 1:
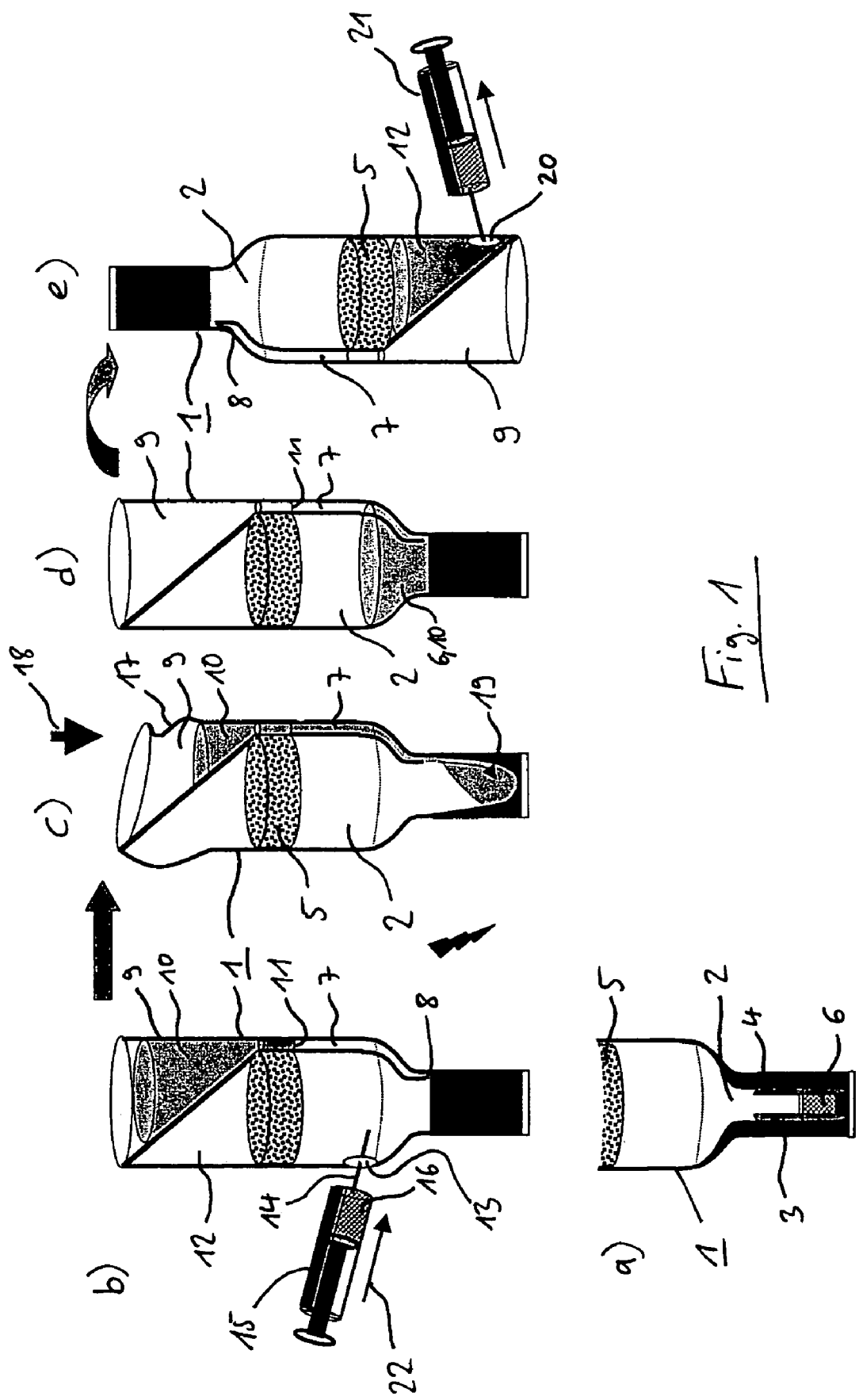
FIG. 1 shows lateral views, partially perspective and partially sectional views, respectively, of a special embodiment of the device according to the invention in respect of different steps of the method according to the invention.

FIG. 1 shows lateral views, partially perspective and partially sectional views, respectively, of a special embodiment of the device according to the invention. In this particularly advantageous embodiment the device according to the invention is a unit which is aseptically sealed and water-proof in all directions, and which allows treatment of cells under perfect aseptic conditions.

FIG. 1a shows a sectional view of the bottom region of the device according to the invention. This region of said device has a chamber 1 which comprises an inner space 2 that serves for receiving biological material, for example a suspension of living cells. Two coplanar electrodes 3, 4 are inserted in this inner space 2, by which the inner space 2 is bordered at two lateral areas in the bottom region of the chamber 1. In the upper region, the chamber 1 comprises a filter 5 which is depicted merely in part in this figure. The filter 5 separates the inner space 2 from another part of the device. The inner space 2 may hold, for example, a buffer solution 6 which may comprise biologically active molecules, e.g. nucleic acids. For example, for use in gene therapy molecules solved in said buffer solution 6 may already be present within the chamber 1. A user merely has to introduce cells which have been recovered from a patient into the inner space 2 of said chamber 1 and then transfer DNA into said cells by generating an electric field.

FIG. 1b shows a lateral perspective view of the device according to the invention as depicted in FIG. 1a, wherein the device is rotated 90° in relation to FIG. 1a. In this representation, the electrode 3 covers the view to the bottom region of the inner space 2. It becomes apparent from this representation that the chamber 1 comprises an inlet line 7 having an opening 8 which is disposed in direct vicinity of the electrodes 3, 4. The chamber 1 is connected to a reservoir 9 in one piece, wherein said reservoir 9 contains a solution 10 for rinsing the inner space 2 of said chamber 1. The chamber 1 and the reservoir 9 are separated from each other by a separating unit 11. This separating unit 11 may be, for example, a valve-like lock or a fragile membrane. Additionally, the chamber 1 is linked to a container 12 in one piece, said container 12 being separated from the inner space 2 of said chamber 1 by the filter 5. Said container 12 and said reservoir 9 each form a unit with said chamber 1, which is aseptically sealed and water-proof in relation to the outside. The chamber 12 further comprises a wall area 13 that can be perforated and through which the canula 14 of a syringe 15 may be inserted into the inner space 2. The syringe 15 may contain, for example, a suspension 16 of living cells, which can be injected into the inner space 2 through the canula 14. The suspension of cells is pressed into the inner space 2 by application of pressure in direction of arrow 22, and is hence available for the following electric treatment. The cells may be, for example, primary cells taken from a patient, which shall be transfected with suitable DNA for gene therapy. A suitable electric field is then generated within the inner space 2 by application of voltage to the electrodes 3, 4, by which DNA can be efficiently transferred into the cells, in particular directly into the nucleus.

FIG. 1c shows the device according to the invention as depicted in FIG. 1b when the inner space 2 of chamber 1 is rinsed after electrically treating the biological material. It becomes apparent from this representation that the wall 17 of the reservoir 9 is made of an elastic material which can be deformed, for example an elastic plastic material. The wall 17 is deformed in direction of arrow 18 by application of pressure on wall 17 and thus pressure is applied to the solution 10 within the reservoir 9. Die to this pressure separating unit 11 between reservoir 9 and chamber 1 can be opened. Alternatively, the separating unit 11 may be opened by another manipulation from the outside. Thus, solution 10 reaches the inner space 2 of chamber 1 via inlet line 7. Since the opening 8 of inlet line 7 is disposed near (in vicinity of) electrodes 3, 4, in particular these electrodes 3, 4 are intensively rinsed by solution 10 with high flow rate. Hereby, the flow rate can be specifically increased by the pressure applied to wall 17. In order to avoid dead volume within inner space 2 the inner surface of chamber wall 19 is designed with rounded nooks so as to allow optimal rinse if inner space 2. Due to this measure treated cells can be suspended almost completely in solution 10. By disposing the opening 8 near both electrodes 3, 4 these are rinsed evenly, wherein turbulances are produced if the distance between both electrodes is small, which are beneficial for the rinsing procedure. Alternatively, the opening may be disposed closer to one electrode which is preferably the cathode. Due to the particularly advantageous construction of the device according to the invention cells adhered to walls and electrodes can be recovered, wherein suspension of cells is ensured even when foam formation occurs if high field strengths are used.

FIG. 1d shows the device according to the invention as depicted in FIG. 1b after the inner space 2 of chamber 1 has been rinsed by solution 10. Rotating the device 180° the solution 10 including the treated cells can reach the container 12 through filter 5. This state is depicted in FIG. 1e. Alternatively, the device according to the invention may already be rotated 180° prior rinsing, wherein a slightly higher pressure has to be applied to solution 10 so as to be pressed at first into the inner space 2 of chamber 1 contrary to gravity. Using the filter 5 larger particles can be retained in the inner space 2 so as to avoid perturbing effects on the treated suspension of cells. As chamber 1 also container 12 has a perforatable wall area 20 through which the suspension of cells may be removed out of said container 12 by means of a syringe 21. The funnel-like shape of the container 12 is thereby beneficial because the cells sedimenting by-and-by are concentrated in the bottom region and thus can be recovered concentrated as well. Accordingly, a sterile suspension of treated cells can be applied to a patient fast, concentrated and in an easy manner.

Figure 2:
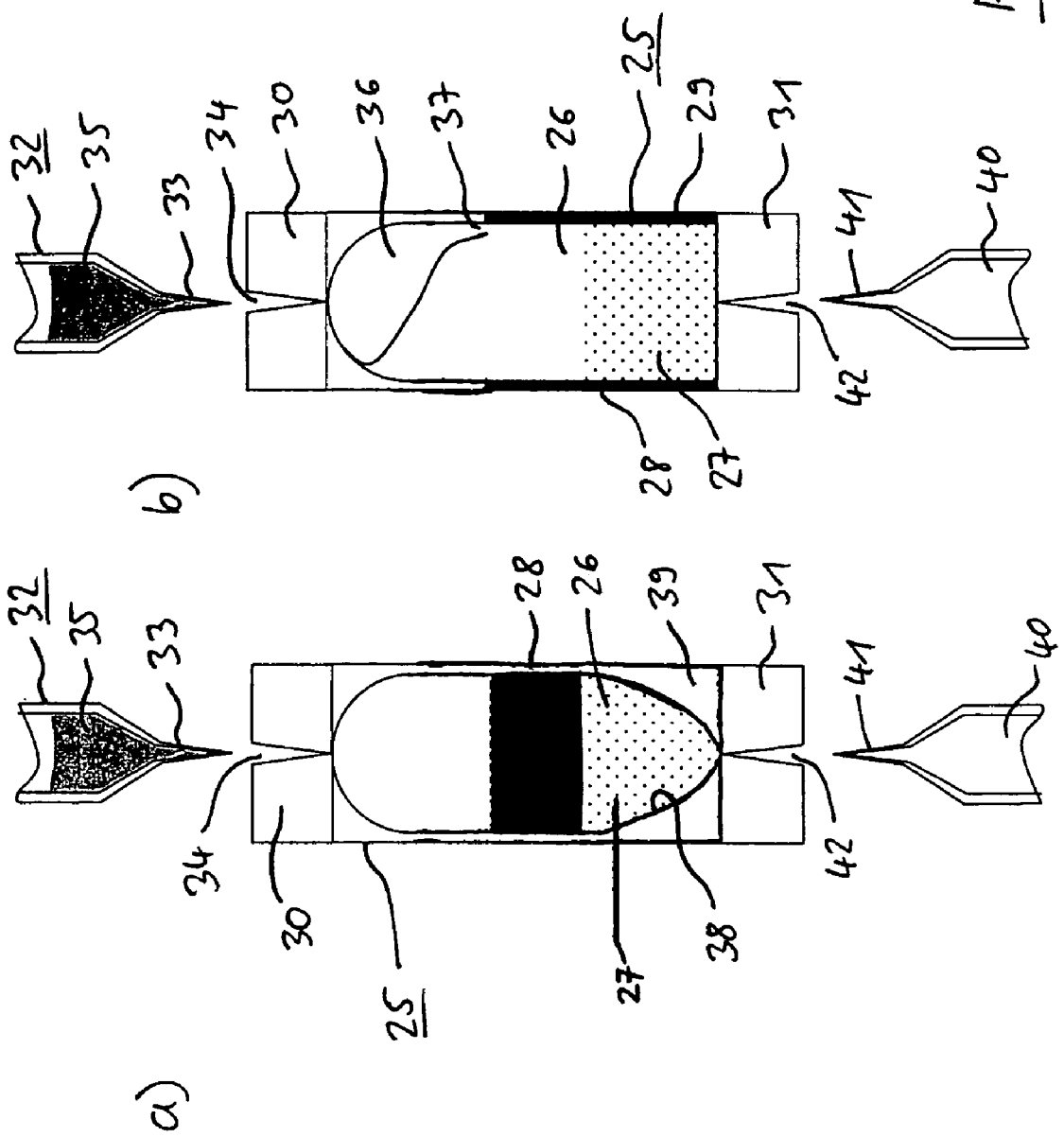
FIG. 2 shows two sectional views of a further embodiment of the device according to the invention, which are rotated 90° in relation to each other.

FIG. 2 shows two sectional views of a further embodiment of the device according to the invention, which are rotated 90° in relation to each other. The device shown comprises a chamber 25 having an inner space 26 which contains a suspension 27 of cells and/or solved biologically active molecules. The chamber 25 further includes two flat electrodes 28, 29 having a plane surface, which are arranged parallel to each other at opposing side walls of said chamber 25. In the representation of FIG. 2a only electrode 28 which is disposed behind the cut surface is visible. The chamber 25 has two connecting members 30, 31 which are disposed at opposing ends of chamber 25. The introduction of cell suspension 27 is accomplished through connecting member 31, preferably from a container having a canula which has a length that corresponds to the thickness of connecting member 31 so that there is no dead volume in the inner space 26 when cells are introduced. The canula may pierce a membrane or the like by which the inner space 26 is sealed in relation to the outside. A reservoir 32 can be connected to connecting member 30, wherein said reservoir 32 may be, for example, a syringe or the like. The reservoir 32 may be elastic and flexible so that its wall can be deformed when, in an alternative embodiment, the solution is sucked out of said reservoir 32 by negative pressure generated by container 40 within inner space 26. The canula 33 of the reservoir 32 can be inserted into a recess 34 of connecting member 30. Said recess 34 may be sealed, for example, by a plug or closed at the passage to inlet line 36 by a valve or a fragile membrane which can be pierced by canula 33. Thus, solution 35 can be transferred from reservoir 32 into inlet line 36 of chamber 25. Said solution 35 reaches the inner space 26 through opening 37 of inlet line 36, wherein electrode 29 is intensely rinsed by said solution 35. Advantageously, electrode 29 is the cathode on which cell material primarily adheres while electroporating cells, which is hardly removable with common devices. As it becomes apparent from FIG. 2a the inner surface 38 of chamber wall 39 is rounded so as to avoid dead volume. In this manner, it is ensured that inner space 26 can be effectively rinsed. Subsequently, the suspension 27 of cells, which is diluted by solution 35, is received by the container 40 so that, in one embodiment, rinsing and removing of cells is accomplished in two steps. Alternatively, the solution can be sucked out of the reservoir 32 through inner space 26 along the electrodes 28, 29 into the container 40 by negative pressure generated by said container 40 within inner space 26 so that here rinsing and removing is accomplished in one step. The canula 41 of the container 40 which may be, for example, a syringe or the like is inserted into a recess 42 of the connecting member 31, as with connecting member 30. Said connecting members 30, 31 may be, for example, Luer locks which can be connected with syringes or infusion pots in commonly known manner. But said connecting members 30, 31 may also be, for example, rubber plugs which can be perforated.

Figures 3, 5:
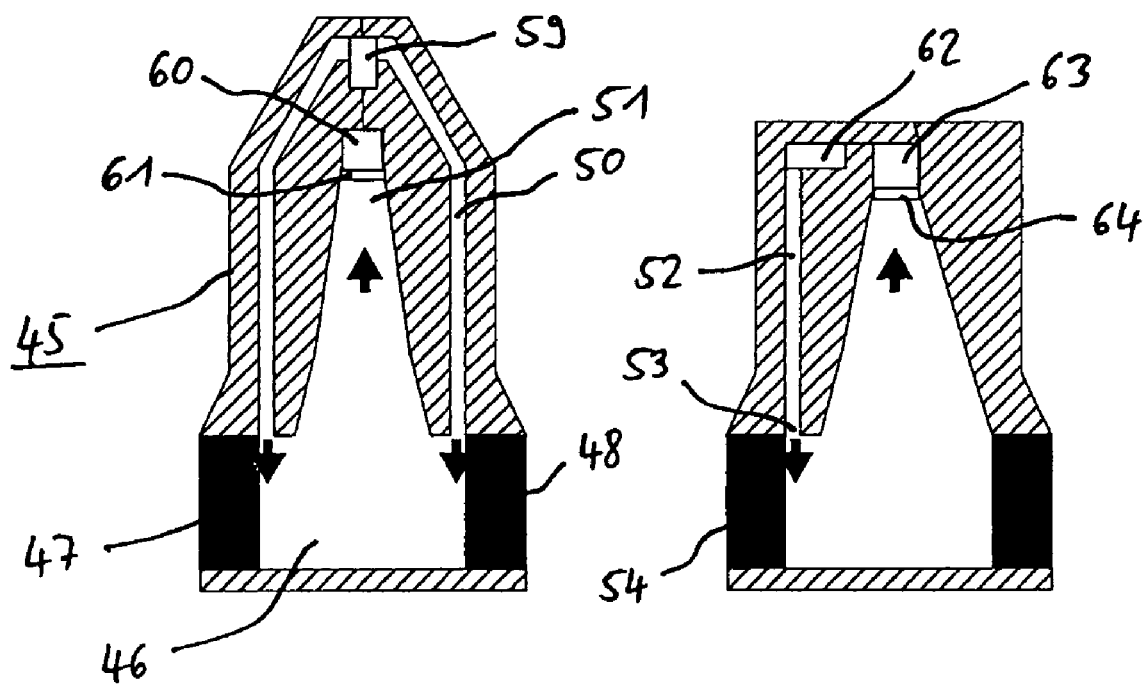
FIG. 3 shows a front sectional view of a further embodiment of the invention.
FIG. 5 shows a front sectional view of an additional alternative embodiment of the device according to the invention.

FIG. 3 shows a front sectional view of a further embodiment of the invention. The device depicted in this representation comprises a chamber 45 including an inner space 46 and two coplanar electrodes 47, 48. This chamber 45 further includes two parallel inlet lines 49, 50 which are disposed in the side areas of chamber 45. Through said inlet lines 49, 50 a solution for rinsing the inner space 46 may be introduced. But said inlet lines 49, 50 may also be used, for example, to introduce the biological material into the inner space 46 and, subsequently, to pour in said solution. The inlet lines are fed via a tube-like overflow, i.e. the oblong overflow channel 59, what is described in detail with respect to FIG. 4. An outlet opening 51 is disposed between both inlet lines 49, 50, through which the content of the inner space 46 of chamber 45 can be recovered. Hereby, the content of said chamber flows into an oblong drain pipeline 60 which is described in detail with respect to FIG. 4. Referring to FIG. 3, a partition member 61 is disposed between the inner space 46 and the drain pipeline 60, which may be, for example, a filter membrane.

Figure 4:
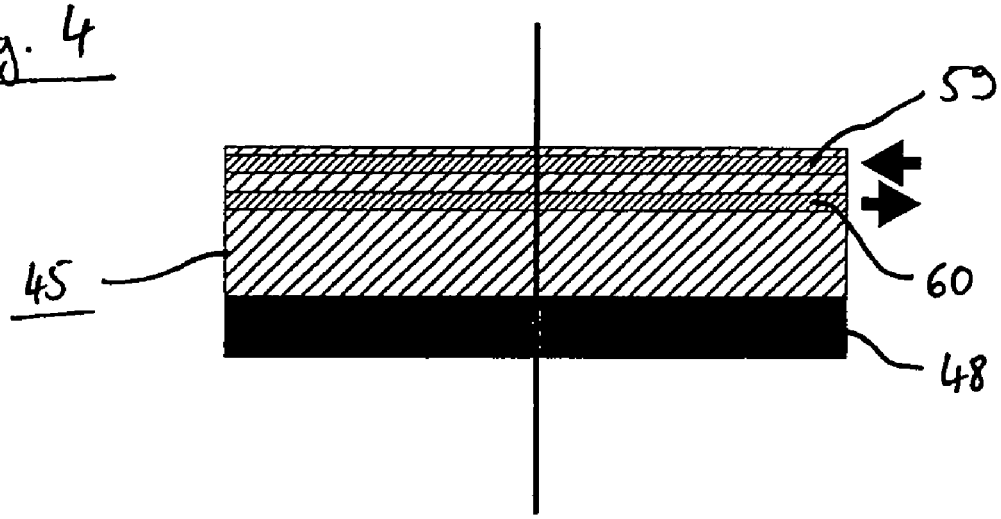
FIG. 4 shows a lateral sectional view of the embodiment according to FIG. 3.

FIG. 4 shows a lateral sectional view of the embodiment according to FIG. 3. Here it becomes apparent that chamber 45 is designed longitudinally extended so as to be suitable for receiving larger volumes. Electrode 48 as well as electrode 47 which is not visible in this representation extend along the entire length of the chamber 45, both electrodes 47, 48 having a minor height. In the inlet area the overflow channel 59 can be connected to a reservoir and a solution is guided through said overflow channel 59 from said reservoir into the inlet lines which are not visible in this representation (reference numbers 49 und 50 in FIG. 3). Said inlet lines extend seam-like along the entire length of the chamber 45 as well. The inlet lines have a smaller cross-section than the overflow channel 59 so that a constant pressure along the entire length of the chamber 45 is produced if the overflow channel 59 is filled with solution. In the outlet area, the drain pipeline 60 which extends parallel to the overflow channel 59 can be connected to a container which receives the treated biological material rinsed out by the solution.

FIG. 5 shows a further alternative embodiment of the invention, which generally corresponds to the device according to FIGS. 3 and 4, wherein in this embodiment only one inlet line 52 is provided. Here, the opening 53 is disposed in direct vicinity of electrode 54 which is preferably the cathode. The inlet line 52 is fed with solution by channel 62, wherein the solution comprising the treated material can be recovered through partition member 64 and channel 62, respectively.

Figure 6:
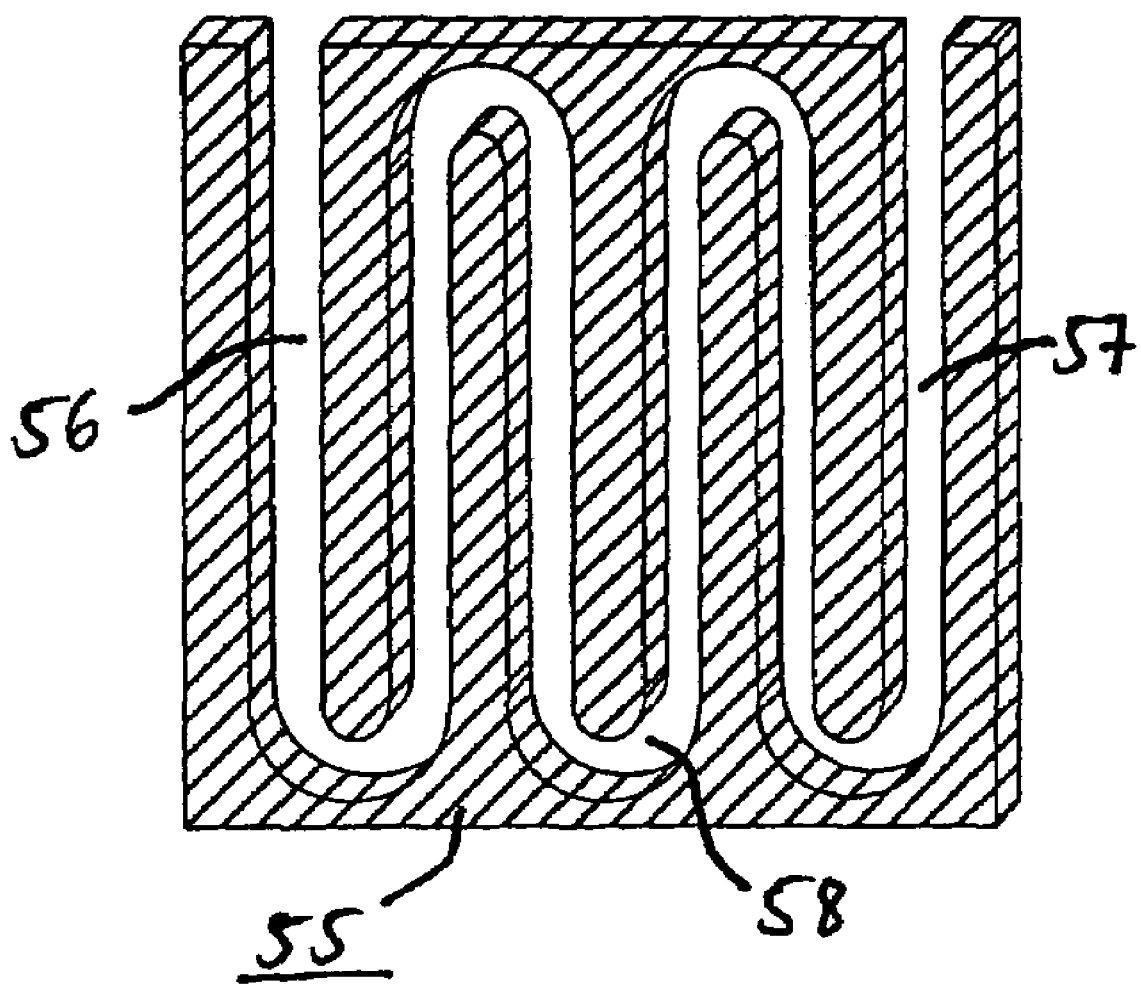
FIG. 6 shows a sectional view of a part of the device according to the invention, including a serpent-like chamber.

FIG. 6 a sectional view of a part of the device according to the invention, including a serpent-like chamber 55. Electrodes are not depicted in this representation but may be disposed in front and behind the cut surface. The chamber 55 includes a tube-like inlet line 56 and a tube-like drain 57 which each are disposed at the ends of the serpent-like inner space 58. Inlet line 56 und inner space 58, respectively, each have an even minor cross-section leading to high flow rate in the inner space 58 and at the surfaces of the electrodes which are not depicted in this representation. Thus, the chamber can be rinsed very effectively and completely. The inner cross-section of inlet line 56 may narrow in direction of inner space 58 so as to increase the flow rate of the solution within said inner space 58.

Figure 7:
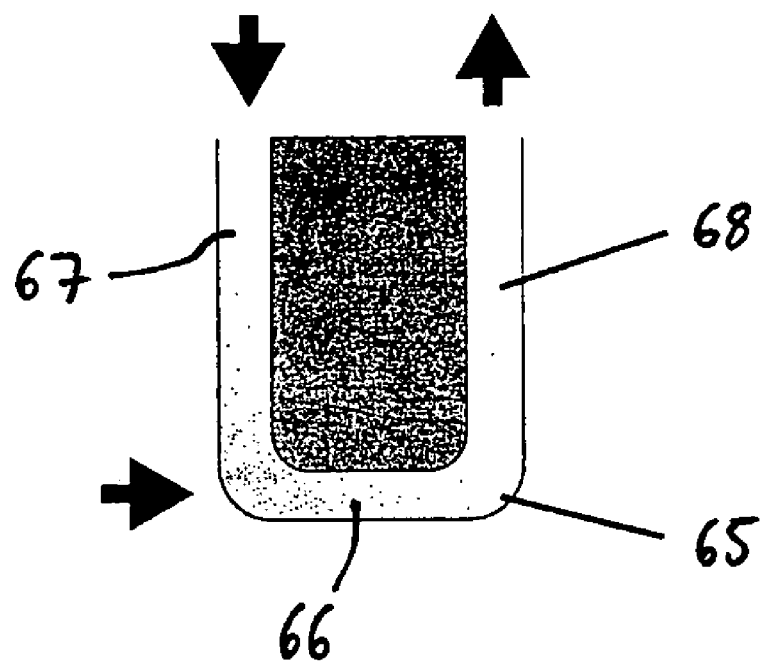
FIG. 7 shows a schematic representation of an embodiment of the invention having a u-shaped chamber.

FIG. 7 shows a further embodiment of the invention having a u-shaped chamber 65. In this embodiment, the electrodes which are not depicted in this representation are disposed in front and behind the cut surface. The solution is introduced into the inner space 66 via inlet line 67, wherein a high flow rate can be achieved due to the minor cross-section of chamber 65. The solution comprising the treated biological material is pressed or sucked out of chamber 65 via drain pipeline 68.

Figure 8:
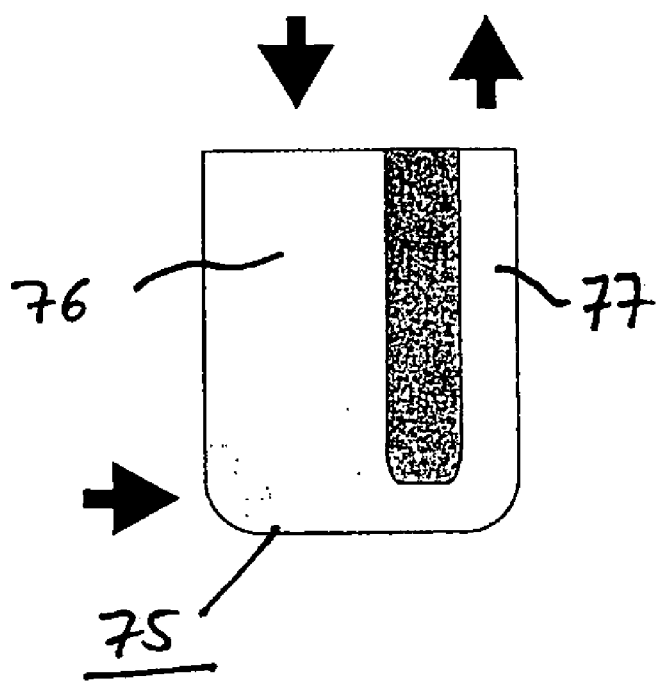
FIG. 8 shows a schematic representation of a further embodiment of the invention.

FIG. 8 shows an alternative embodiment of the invention, which generally corresponds to the embodiment according to FIG. 7. However, in this embodiment the inlet line 76 of the chamber 75 has a significantly larger cross-section than the drain pipeline 77 so that larger volumes can be processed.

LIST OF REFERENCE NUMBERS

1 Chamber
2 Inner space
3 Electrode
4 Electrode

5 Filter
6 Buffer solution
7 Inlet line
8 Opening
9 Reservoir
10 Solution
11 Separating unit
12 Container
13 Wall area
14 Canula
15 Syringe
16 Suspension
17 Wall
18 Arrow
19 Chamber wall
20 Wall area
21 Syringe
22 Arrow
25 Chamber
26 Inner space
27 Suspension
28 Electrode
29 Electrode
30 Connecting member
31 Connecting member
32 Reservoir
33 Canula
34 Recess
35 Solution
36 Inlet line
37 Opening
38 Surface
39 Chamber wall
40 Container
41 Canula
42 Recess
45 Chamber
46 Inner space
47 Electrode
48 Electrode
49 Inlet line
50 Inlet line
51 Outlet opening
52 Inlet line
53 Opening
54 Electrode
55 Chamber
56 Inlet line
57 Drain
58 Inner space
59 Overflow channel
60 Drain pipeline
61 Partition member
62 Channel
63 Channel
64 Partition member
65 Chamber
66 Inner space
67 Inlet line
68 Drain pipeline
75 Chamber
76 Inlet line
77 Drain pipeline

What is claimed is:

1. Device for treating biological material comprising at least one chamber which at least can be closed to the outside, said chamber comprising an inner space for receiving said biological material, at least one electrode for generating an electric field and which is in contact with said inner space of said chamber, at least one inlet line which comprises at least one opening which is disposed close to said electrode, wherein at least one reservoir for receiving a solution, which is formed by a wall, is connectable or connected to said inner space via said inlet line, and wherein said inner space of said chamber and said reservoir are separated from each other by a separating unit which is designed so that a separation created by said separation unit can be broken by extraneous mechanical impact, and a container, wherein said container is at least connectable to or connected to an outlet opening of said chamber or connectable to said chamber via a connecting member.

2. The device of claim 1, wherein the inner diameter of said inlet line decreases in the direction of said electrode.

3. The device of claim 1, wherein said separating unit is a valve or a fragile membrane which can be destroyed by applying pressure.

4. The device of claim 1, wherein said chamber is at least aseptically sealed to the outside.

5. Device for treating biological material comprising at least one chamber which at least can be closed to the outside, said chamber comprising an inner space for receiving said biological material, at least one electrode for generating an electric field and which is in contact with said inner space of said chamber, at least one inlet line which comprises at least one opening which is disposed close to said electrode, wherein at least one reservoir for receiving a solution, which is formed by a wall, is connectable or connected to said inner space via said inlet line, and wherein said inner space of said chamber and said reservoir are separated from each other by a separating unit which is designed so that a separation created by said separation unit can be broken by extraneous mechanical impact, wherein said wall forming said reservoir comprises an elastic and/or deformable material, and a container, wherein said container is at least connectable to or connected to an outlet opening of said chamber or connectable to said chamber via a connecting member.

6. The device of claim 1, wherein said reservoir is at least connected to said chamber forming one piece with the chamber or connectable to said chamber via a connecting member.

7. The device of claim 6, wherein said chamber and said reservoir form a unit which is at least aseptically sealed to the outside.

8. The device of claim 1, wherein said chamber comprises at least one wall area which is self-sealing and can be perforated or which is equipped with at least one inlet comprising a connecting member.

9. The device of claim 1, wherein said chamber is divided into several subunits by at least one dividing member.

10. The device of claim 9, wherein said dividing member comprises a valve and/or a filter.

11. The device of claim 1, wherein said container is connected to said chamber forming one piece with said chamber.

12. The device of claim 1, wherein a partition member is disposed between said chamber and said container.

13. The device of claim 12, wherein said partition member is a valve or a filter.

14. The device of claim 1, wherein said container comprises at least one wall area which is self-sealing and can be perforated or which is equipped with at least one outlet comprising a connecting member.

15. The device of claim 1, wherein said container and said chamber form a unit which is aseptically sealed to the outside.

16. The device of claim 8, wherein said wall area which is self-sealing and can be perforated comprises a synthetic material.

17. The device of claim 1,
wherein said chamber comprises two oppositely arranged electrodes which are in contact with said inner space, or
wherein a further electrode can be introduced into said inner space of said chamber.

18. The device of claim 1, wherein said electrode or electrodes comprise(s) an electro-conductive synthetic material.

19. The device of claim 18, wherein said electro-conductive synthetic material is a plastic material which is doped with conductive material.

20. A method for treating biological material comprising:
providing an inner space of a chamber which at least can be closed to an outside, said inner space comprising
at least one electrode which is placed in contact with said inner space of said chamber for generating an electric field in said inner space after introducing said biological material by applying voltage to said electrode and a further electrode which is in contact with said inner space of said chamber,
introducing said biological material into said inner space of said chamber,
after generating the electric field, almost completely rinsing said biological material out of said inner space of said chamber with a solution, said solution being guided from a reservoir containing said solution via an inlet line of said chamber along at least one electrode and said reservoir being connected or connectable to said chamber via said inlet line, wherein said inlet line comprises at least one opening which is disposed close to said electrode, and
wherein a separating unit which separates said inner space of said chamber from said reservoir is opened by extraneous mechanical impact, and
wherein said biological material and said solution, respectively, are introduced into a container which is at least connectable to an outlet opening of said chamber or connectable to said chamber via a connecting member.

21. The method of claim 20, wherein said solution is guided along said electrode under pressure.

22. The method of claim 20, wherein said biological material is introduced into said inner space of said chamber with a syringe or a syringe-like device through a wall area which is self-sealing and can be perforated.

23. The method of claim 20, wherein said separating unit is a valve which can be opened by extraneous mechanical impact at least in one direction, or a fragile membrane which can be destroyed by extraneously applied pressure.

24. The method of claim 20, wherein said reservoir which contains said solution is at least partially formed by an elastic and/or deformable wall and a pressure is extraneously applied to said wall.

25. The method of claim 20, wherein said biological material is rinsed into said container through a partition member, which is disposed between said chamber and said container.

26. The method of claim 25, wherein said partition member is a valve and/or filter.

27. The method of claim 23, wherein treated biological material is removed from said container using a syringe or syringe-like device through a wall area which is self-sealing and can be perforated.

28. The method claim 20, wherein said biological material comprises living cells, derivatives of cells, sub-cellular particles and/or vesicles, into which biologically active molecules are transferred by generation of said electric field, or which are fused by generation of said electric field.

29. The method of claim 28, wherein said biologically active molecules are dissolved in a buffer solution and introduced into the inner space of said chamber before the biological material is added.

30. The method of claim 28, wherein the transfer of said biologically active molecules into said living cells is achieved via a current density of up to 120 A/cm$^2$, preferably 80 A/cm$^2$, or by a voltage pulse having a field strength of 2-10 kV*cm$^{-1}$ and a duration of 10-200 µs.

31. The method of claim 30, wherein the transfer of said biologically active molecules into said living cells is achieved by a current flow following said voltage pulse without interruption, said current flow having a current density of 2-14 A/cm$^2$, preferably 5 A/cm$^2$, and a duration of 1-100 ms, preferably 50 ms.

* * * * *